United States Patent [19]
Nicolaisen et al.

[11] Patent Number: 5,580,560
[45] Date of Patent: Dec. 3, 1996

[54] MODIFIED FACTOR VII/VIIA

[75] Inventors: Else M. Nicolaisen, Frederiksberg; Søren E. Bjørn, Lyngby; Finn C. Wiberg, Farum, all of Denmark; Richard Woodbury, Dover, N.H.

[73] Assignee: Novo Nordisk A/S, Bagsvaerd, Denmark

[21] Appl. No.: 293,778

[22] Filed: Aug. 22, 1994

Related U.S. Application Data

[63] Continuation of Ser. No. 104,509, Aug. 9, 1993, abandoned, which is a continuation-in-part of Ser. No. 898,248, Jun. 12, 1992, abandoned, which is a continuation of Ser. No. 434,149, Nov. 13, 1989, abandoned.

[51] Int. Cl.$^6$ ............ A61K 38/48; C12N 9/48; C12N 15/57; C12N 5/10
[52] U.S. Cl. ............ 424/94.64; 435/212; 435/226; 435/240.2; 536/23.2
[58] Field of Search ............ 530/384; 435/69.6, 435/320.4, 240.1; 514/8, 12; 536/23.2

[56] References Cited

U.S. PATENT DOCUMENTS

| | | | |
|---|---|---|---|
| 4,479,938 | 10/1984 | Thomas | 424/101 |
| 4,784,950 | 11/1988 | Hagen et al. | 435/69.6 |
| 5,187,157 | 2/1993 | Kettner et al. | 514/18 |
| 5,288,629 | 2/1994 | Berkner | 435/240.2 |
| 5,405,946 | 4/1995 | Griffin et al. | 530/380 |

FOREIGN PATENT DOCUMENTS

| | | |
|---|---|---|
| 0161937 | 11/1985 | European Pat. Off. |
| 0201153 | 11/1986 | European Pat. Off. |
| 0200421 | 12/1986 | European Pat. Off. |
| 0225160 | 6/1987 | European Pat. Off. |
| 0233013 | 8/1987 | European Pat. Off. |
| 86/01438 | 3/1986 | WIPO |
| 88/10295 | 12/1988 | WIPO |

OTHER PUBLICATIONS

Radclife et al. 1975. J. Biol. Chem, 250(2): 388–395.
Abstract (WPI Accession No.: 89023839/03) of Bjorn et al. WO 88 10295, Dec. 29, 1988.
Broze et al. 1985. J. Clin. Invest, 76: 937–946.
Wilkenson, J. M. 1986. *Practical Chemistry: A Handbook*, John Wiley & Sons Ltd., London, UK, pp. 122–147.
Dayhoff et al. 1972, *Altar of Protein Sequence and Structure*, 5:89–99.
Eaton et al. 1986, Biochemistry 25:505–512.
Hagen et al. 1986, Proc. Natl. Acad. Sci. 83:2412–2416.
Broze et al., J. Biol. Chem., vol. 255, No. 4, pp. 1242–1247, 1980.
Merrifield, B., Science, vol. 232, pp. 341–347, 1986.
Kaiser et al., Science, vol. 243, pp. 187–192, 1989.
Hedner and Kisiel, J. Clin. Invest. vol. 71, pp. 1836–1841, 1983.
Pongor, S., Methods in Enymology vol. 154, pp. 450–473, 1987.
Creighton, Proteins Structures and Molecular Principles, pp. 93–98, 1983.
Kisiel et al., Behring Inst. Mill No. 73, pp. 29–42, 1983.
Nemerson and Repke, Thromb. Res., vol. 40, pp. 351–358, 1985.
Turkington, Haemostasis, vol. 24, pp. 111–116. 1991.
Turkington, Thromb. Res., vol. 63, pp. 399–406, 1991.
Pederson et al., Biochemistry, vol. vol. 28, pp. 9331–9336, 1989.
Sakai et al., J. Biol. Chem. vol. 265, pp. 1890–1985, 1990.
Tanaka et al., Biochemistry, vol. 24, pp. 2040–2047, 1985.
Jesty et al., J. Biol. Chem., vol. 250, pp. 4497–4505, 1975.
A. Darbe (Eds.), John Wiley & Sons, Ltd., pp. 121–147 (1986).

*Primary Examiner*—Dian C. Jacobson
*Assistant Examiner*—Eric Grimes
*Attorney, Agent, or Firm*—Steve T. Zelson, Esq.; Cheryl H. Agris, Esq.

[57] ABSTRACT

This application relates to modified blood coagulation factors, DNA sequences coding for such modified factors and a process for their production.

15 Claims, 8 Drawing Sheets

γ = gamma-carboxyglutamic acid
β = beta-hydroxy-aspartic acid
∿ glucosylation sites
→ activation site (F XII$_a$)
∗ active site residues
⇢ proteolytic cleavage sites

FIG. 8

ε
278
Val-Arg-Phe-Ser-Leu-Val-Ser-Gly-Trp-Gly-Gln-Leu-Leu-Asp-Arg-Gly-Ala-Thr-Ala (SEQ ID NO:25)

γ
290

β
315
Gln-Ser-Arg-Lys-Val-Gly-Asp-Ser-Pro-Asn-Ile-Thr-Glu-Tyr-Met-Phe-Cys-Ala-Gly-Tyr-Ser-Asp-Gly-Ser (SEQ ID NO:26)

δ
332

MODIFIED FACTOR VII/VIIA

This application is a continuation application of application Ser. No. 08/104,509, filed Aug. 9, 1993, now abandoned, the contents which are incorporated herein by reference, which is a continuation-in-part of, U.S. patent application Ser. No. 07/898,248, now abandoned, filed Jun. 12, 1992, which is a continuation of U.S. patent application Ser. No. 07/434,149, now abandoned, filed Nov. 13, 1989.

FIELD OF THE INVENTION

The present invention is related to modified factor VII/VIIa's, DNA sequences coding for such modified factors and a process for their production. The invention is further related to pharmaceutical compositions comprising such modified factors and their uses.

BACKGROUND OF THE INVENTION

Factor VIIa is a serine protease that participates in blood coagulation by activating factor X and/or factor IX. Factor VIIa is produced from its precursor, factor VII (FVII), which is synthesized in the liver and secreted into the blood where it circulates as a single-chain glycoprotein (MW=50,000).

Factor VII can in vitro be converted into the two-chain form factor VIIa by factor Xa, factor XIIa, factor IXa or thrombin. Several coagulation enzymes are capable of activating FVII, a process which is greatly enhanced by the binding to tissue factor and negatively charged phospholipids A (Nemerson and Repke, 1985, Thromb. Res. 40:351–358 and Silverberg et al., 1977, J. Biol. Chem. 252:8481–8488). Single chain FVII is converted to the two chain form, when bound in sufficient density to charged surfaces, (Radcliffe and Nemerson, 1975, J. Biol. Chem. 250:388–395 and Bjoern and Thim, 1986, Res. Discl. 269: 564–565) and evidence for autoactivation has been presented (Pederson et al., 1989, Biochemistry 28:9331–9336).

In the presence of tissue factor and calcium ions, factor VIIa, in vivo, is believed to convert factor X (FX) to factor Xa (FXa) by limited proteolysis. The latter enzyme in turn converts prothrombin to thrombin in the presence of factor Va (FVa), calcium ions, and phospholipid. Factor VIIa will also convert factor IX (FIX) to factor IXa (FIXa) in the presence of tissue factor and calcium.

Factor VII can be purified from plasma and activated into factor VIIa by for example, methods described by Broze and Majerus, 1980, J. Biol. Chem. 255: 1242–1247 and Hedner and Kisiel, 1983, J. Clin. Invest. 71:1836–1841. Factor VIIa may also be produced by recombinant DNA technology by culturing in an appropriate medium mammalian cells transfected with a DNA-sequence encoding factor VII, isolating the protein produced and activating said protein to factor VIIa (see, for example, European patent application no. 86302855.1).

The cDNA coding for human factor VII has been characterized (Hagen et al., 1986, Proc. Natl. Acad. Sci. U.S.A., 83: 2412–2416). The amino acid sequence deduced from the cDNAs indicates that factor VII is synthesized with a prepro-leader sequence of 60 or 38 amino acids. The mature factor VII that circulates in plasma is composed of 406 amino acid residues. The amino acid sequence analysis of the activated protein and the amino acid sequence deduced from the cDNAs indicate that factor VII is converted to factor VIIa by the cleavage of a single peptide bond between arginine (152) and isoleucine (153). This results in the formation of a two-chained molecule consisting of a light chain (152 amino acid residues) and a heavy chain (254 amino acid residues) that are held together by one disulphide bond. The light chain contains a γ-carboxyglutamic acid (Gla) domain and two potential epidermal growth factor domains, while the heavy chain contains the serine protease portion of the molecule.

Biosynthesis of functional coagulation factor VII requires a vitamin K dependent posttranslational γ-carboxylation of 10 glutamic acid residues in the N-terminal part of the molecule (Hagen et al., 1986, Proc. Natl. Acad. Sc. U.S.A. 83:2412–2416). The Gla-domain is involved in the $Ca^{2+}$ dependent binding of FVII to negatively charged phospholipids associated with cell surface bound tissue factor (Sakai et al., 1990, J. Biol Chem., 265:1890–1894). Binding strongly promotes the conversion of the FVII zymogen to FVIIa, and also the enzymatic activity of FVIIa towards its substrates, FIX and FX, is profoundly enhanced (Nemerson and Repke, 1985, Thromb. Res. 40:351–358 and Silverberg et al., 1977, J. Biol. Chem. 252:8481–848).

Factor VIIa may be used in treating patients who have developed inhibitors to factor VIII (Hedner and Kisiel, 1983, J. Clin. Invest. 71:1836–1841) and for the treatment of patients suffering from bleeding disorders such as platelet disorders including thrombocytopenia, von Willebrand's disease and others typically present in association with severe tissue damages (European patent application no. 86309197.1).

Factor VIIa has been found to be a protein susceptible to proteolytic cleavage giving rise to a number of degradation products without clotting activity. Factor VII contains 17 lysine (positions 18, 32, 38, 62, 85, 109, 137, 143, 148, 157, 161, 197, 199, 316, 337, 341, 389) and 24 arginine (positions 9, 15, 28, 36, 79, 110, 113, 144, 152, 202, 223, 224, 247, 266, 271, 277, 290, 304, 315, 353, 379, 392, 396, 402) residues that are all susceptible to proteolytic degradation. The proteolytic cleavage may occur at different steps of the recovery procedure and also during storage. Degradation products have been observed both for factor VIIa derived from plasma as well as for factor VIIa produced by recombinant DNA technology.

As the degradation products are inactive molecules, their occurrence in the factor VIIa preparation will lead to a lower specific activity of the final preparation. Furthermore, the amount and nature of the degradation products may vary from one production batch to another giving rise to preparations with a variable content of biologically active factor VIIa.

One such proteolytic enzyme, cathepsin G, is a serine protease with chymotrypsin-like activity from human granulocytes (neutrophils), involved in connective tissue degradation. When the neutrophils are activated by external stimuli, these active proteinases are secreted. Systemic activation and excessive release of cathepsin G occurs in various diseased states such as septicemia and leukemia. The abnormal hemostatic balance observed under these conditions may result from cathepsin G mediated cleavage of the Gla-domains of coagulation factors. The enzyme cleaves predominantly after aromatic residues, with a substantial preference for Phe (Tanaka et al., 1985, Biochemistry 24:2040–2047).

Cathepsin G cleaves human FX and protein C between Phe-40 and Trp-41 (Turkington, 1991, Haemostasis 21:111–116 and Turkington, 1991, Thromb. Res. 63:399–406). This sequence is also present in FVII. The homologous position in human protein C contains a His, in contrast to the other vitamin K dependent coagulation enzymes. Human FX has, adjacent to Tyr-44, a lysine residue, which might lower the affinity for the cathepsin G (Tanaka et al., 1985, Biochemistry 24:2040–2047).

Factor VIIa preparations containing inactive degradation products will as mentioned have a less specific activity as compared to preparations in which all or a major part of the protein material is active. Accordingly, higher and more frequent doses are necessary to obtain and sustain a therapeutic or prophylactic effect as compared to a preparation with higher specific activity.

Variable amounts of inactive degradation products and as a consequence, variable content of biologically active factor VIIa will furthermore make calculation of appropriate doses troublesome and difficult, if not in some circumstances impossible.

Finally, a content of non-physiological degradation products in the final preparation may trigger the immune system of the patient. Re-administration may then result in allergic reactions, which in severe cases may have a lethal course. Patients may also develop high titers of antibodies against factor VIIa rendering subsequent treatment difficult or ineffective. Accordingly, a factor VIIa preparation with less tendency to proteolytic degradation in vitro will be more satisfactory and potentially more useful in factor VIIa therapy.

Although the exact half-life of factor VIIa is unknown, preliminary results suggest that factor VIIa procoagulant activity is rapidly cleared from the bloodstream upon intravenous administration (Hedner and Kisiel, 1983, Clin. Invest. 71:1836–1841).

The treatment and the lives of the patients will be negatively influenced by the observed short in vivo half life of native factor VIIa. Relatively high doses and frequent administration will be necessary to reach and sustain the desired therapeutic or prophylactic effect. As a consequence, adequate dose regulation will be difficult to obtain and the need for frequent intravenous administrations will impose restrictions on the patients' way of living.

Therefore, a need exists in the art for factor VIIa preparations which are stable during production, purification and storage even at high concentrations, and which furthermore have a longer half life and slower clearance from the blood than the native or recombinant factor VIIa. The present invention fulfills this need by providing certain modified factor VII/VIIa.

SUMMARY OF THE INVENTION

In its broadest aspect, the present invention provides a modified factor VII/VIIa being stabilized against proteolytic cleavage at certain positions in the molecule. More specifically, the present invention provides modified factor VII/VIIa in which one or more proteolytically sensible peptide bond(s) in native factor VII/VIIa has/have been replaced by a proteolytically more stable peptide bond.

According to the present invention, this is achieved by modifications at certain positions in the native human factor VII/VIIa molecule. Such modifications may include removal of certain amino acid residues or replacement of one or more amino acid residues with a different amino acid residue. For instance, a trypsin-like proteolytic cleavage my be hindered by stabilizing the peptide bond on the C-terminal end of certain Arg and/or Lys residues and/or replacement of certain Arg and/or Lys residues with other amino acid residues and/or by removal of certain Arg and/or Lys residues.

In a specific embodiment, modifications are made at one or more of the following trypsin-like cleavage sites:
(i) lysine(38)-leucine(39)
(ii) lysine(32)-aspartate(33),
(iii) arginine(290)-glycine(291),
(iv) arginine(315)-lysine(316),
(v) lysine(341)-glycine(342),
(vi) arginine(304)-leucine(305)

In another embodiment, a chymotrypsin-like cleavage site(s) is modified. Furthermore, in yet another embodiment, the chymotrypsin-like site that is modified is a cathepsin G site. In a specific embodiment, the chymotrypsin-like site(s) is selected from the group consisting of:
(vii) isoleucine(42)-serine(43),
(viii) tyrosine(44)-serine(45),
(ix) phenylalanine(278)-serine(279),
(x) tyrosine(332)-serine(333)

In a preferred embodiment, the cleavage sites modified are (i), (ii), (iii) and (iv) have been found to be the ones most susceptible to proteolytic degradation, while the remaining are of less quantitative importance.

When considering the stabilization of factor VII/VIIa, it is an important aspect that the resulting modified factor VII should retain its activity. This is according to the invention obtained by comparing the sequence of native factor VII/VIIa in the area to be modified with corresponding sequences in related proteins such as factor IX, factor X, factor II and protein C. Homologous sequences around the major cleavage sites are shown below:

| | | |
|---|---|---|
| Factor II | 32      38 42 44<br>|        |   |  |<br>E E A F E A L E S S T A T D V F W A K Y T A – | (SEQ ID NO: 1) |
| Factor VII | E E A R E I F K D A E R T K L F W I S Y S D G | (SEQ ID NO: 2) |
| Factor X | E E A R E V F E D S D K T N E F W N K Y K D G | (SEQ ID NO: 3) |
| Factor IX | E E A R E V F E B T E R T T E F W K O Y V D G | (SEQ ID NO: 4) |
| Protein C | E E A K E I F Q N V D D T L A F W S K H V D G | (SEQ ID NO: 5) |
| Factor II | 278                290<br>|                  |<br>G Y K G R V T G W G N L K E T W T A N V G K G Q P S V – L | (SEQ ID NO: 6) |
| Factor VII | V R F S L V S G W G Q L – – – – – – – L D R G A T A L E L | (SEQ ID NO: 7) |
| Factor X | Q K R G I V S G F G R T – – – – – – – H E K G R Q S T R L | (SEQ ID NO: 8) |
| Factor IX | F G S G Y V S G W G R V – – – – – – – F H K G R S A L V L | (SEQ ID NO: 9) |
| Protein C | G Q E T L V T G W G Y B – – – – – – – S S R E K E A K R N | (SEQ ID NO: 10) |

| | | | | |
|---|---|---|---|---|
| Factor II | 315 | 332 | 341 | (SEQ ID NO: 11) |
| | C-KDSTRI----RI TDNMF CAGYKP DEGKRGDACE GDS GGP F | | | |
| Factor VII | CLQQS RKVGDS PNI TEYMF CAGYS--DGS K-DS CKGDS GGP H | | | (SEQ ID NO: 12) |
| Factor X | C-----KLSSSFI I TQNMF CAGYD--TKQE-DACQGDS GGP H | | | (SEQ ID NO: 13) |
| Factor IX | CLR-STKFT----I YNNMF CAGFH--EGGR-DS CQGDS GGP H | | | (SEQ ID NO: 14) |
| Protein C | CSEVMSNM------VSENML CAGI L--DGRQ-DACEGDS GGP M | | | (SEQ ID NO: 15) |

Consequently, it is an object of the present invention to provide for modified factor VII/VIIa wherein one, more or all of the lysine, arginine, isoleucine, phenylalanine and tyrosine residues:
(i) lysine(38)
(ii) lysine(32)
(iii) arginine(290)
(iv) arginine(315)
(v) lysine(341)
(vi) arginine(304)
(vii) isoleucine(42)
(viii) tyrosine(44)
(ix) phenylalanine(278),
(x) tyrosine(332)
have been stabilized by substitution and/or deletion.

In a preferred embodiment of the invention, one, more or all of the amino acid residues in positions (32), (38), (278), (290), (315), and (332) have been stabilized by substitution or deletion.

According to the present invention, Lys in position 32 (ii) and/or 38 (i) may be replaced by another amino acid residue. Lys(38) may preferably be replaced by Thr, Asp, Leu, Gly, Ala, Ser, Asn or His and Lys(32) may preferably be replaced by Gln, Glu, His, Gly, Thr, Ala, or Ser.

Also, Arg in position 290 (iii) may be replaced by another amino acid residue, for instance Gly, Ala, Ser, Thr or Lys, preferably Ser, Ala or Gly.

Arg(315) (iv) and Arg(304) (x) may preferably be substituted by Gly, Thr, Ala, Ser or Gln.

Furthermore, Lys(341) (vii) may be substituted by Glu, Gln, Gly, Thr, Ala or Ser, preferably Glu or Gln.

Phe in position 278 and Tyr in position 332 may be replaced with Ser, Ala, Gly, Asn, Gln.

Besides substitution of the above-mentioned Arg or respective Lys residues with another amino acid residue, removal of the Arg or Lys amino acid residues may also be considered in order to avoid proteolytic cleavage. Furthermore, one or more of the amino acid residues on either the N- or C-terminal side of such Arg or Lys residues may be substituted by another amino acid residue exerting a stabilizing effect on the proteolytically sensible peptide bond. An example of such modifications is substitution of the amino acid residue linked to the C-terminal end of a Lys or Arg residue with Pro.

To avoid proteolytic cleavage at position 42 (vii) and 44 (viii), Ile(42), and/or Tyr(44) may be substituted by Asn, Ser, Ala or Gln.

The present invention is contemplated to cover any combination of the above-mentioned substitutions and deletions.

The invention is also directed to a recombinant DNA molecule comprising a DNA sequence encoding modified factor VII/VIIa and a method for obtaining such a recombinant DNA molecule.

The invention is further directed to a method for obtaining a modified Factor VII. The method comprises the following steps:

(a) transforming a cell with a recombinant DNA molecule comprising a DNA sequence encoding a modified factor VII;

(b) culturing the transformed cell of step (a); and (c) isolating the modified factor VII expressed in the cultured cell of step(b).

Modified factor VIIa can be obtained by activating modified factor VII.

The invention is further directed to pharmaceutical compositions comprising the modified factor VII/VIIa of the present invention and a pharmaceutically acceptable carrier. Furthermore, the invention is directed to a method for treatment of a bleeding disorder.

Other aspects of the invention will become evident upon reference to the following detailed description and attached drawings.

DEFINITIONS

Prior to setting forth the invention, it may be helpful to an understanding thereof to set forth definitions of certain terms to be used hereinafter.

Complementary DNA or cDNA: A DNA molecule, or a clone of such a molecule, either single- or double-stranded, which may be isolated in partial form from a naturally occurring gene or which has been modified to contain segments of DNA which are combined and juxtaposed in a manner which would not otherwise exist in nature.

Plasmid or Vector: A DNA construct containing genetic information which may provide for its replication when inserted into a host cell. A plasmid generally contains at least one gene sequence to be expressed in the host cell, as well as sequences encoding functions which facilitate such gene expression, including promoters and transcription initiation sites. It may be a linear or closed circular molecule. As used herein, the term "expression vector" shall mean a plasmid or vector containing a transcription promoter and terminator operably linked to a DNA sequence encoding a protein or polypeptide of interest. Expression vectors may further contain other elements, including selectable markers, enhancers, polyadenylation signals, etc., which will be determined in part by the particular host cell chosen.

Biological Activity: A function or set of functions performed by a molecule in a biological context (i.e. in an organism or an in vitro facsimile). Biological activities of proteins may be divided into catalytic and effector activities. Catalytic activities of clotting factors generally involve the activation of other factors through the specified cleavage of precursors. Effector activities including specific binding of the biologically active molecule to calcium or other small molecules, to macromolecules such as proteins or to cells. Effector activity frequently augments, or is essential to, catalytic activity under physiological conditions. Catalytic and effector activities may, in some cases, reside within the same domain of a protein.

For factor VIIa, biological activity is characterized by the mediation of blood coagulation through the extrinsic pathway. Factor VIIa activates factor X to factor Xa, which in turn converts prothrombin to thrombin thereby initiating the formation of a fibrin clot.

The modified factor VIIa according to the present invention has a biological activity that is substantially the same as that of native factor VIIa.

"Factor VII/VIIa" as used in this application means a product consisting of either the unactivated form (factor VII) or the activated form (factor VIIa) or mixtures thereof. "Factor VII/VIIa" within the above definition includes proteins that have the amino acid sequence of native human factor VII/VIIa. It also includes proteins with a slightly modified amino acid sequence, for instance, a modified N-terminal end including N-terminal amino acid deletions or additions so long as those proteins substantially retain the activity of factor VIIa. "Factor VII" within the above definition also includes natural allelic variations that may exist and occur from one individual to another. Also, degree and location of glycosylation or other post-translation modifications may vary depending on the chosen host cells and the nature of the host cellular environment.

"Modified factor VII/VIIa" shall mean a biologically active molecule derived from factor VII/VIIa by the substitution or deletion of one or more amino acid residues.

As the modifications according to the present invention are made on the gene expression level, modifications introduced in the factor VII molecule will also be found in the activated product (factor VIIa).

The number system of the amino acid sequence of factor VII/VIIa used herein appears from FIG. 1 in which the N-terminal alanine is numbered 1 and the C-terminal proline is numbered 406.

The three letter and one letter abbreviations used for the amino acids are those as normally used in the art, i.e.:

| Amino Acid | Three letter abbreviation | One letter abbreviation |
| --- | --- | --- |
| Alanine | Ala | A |
| Cysteine | Cys | C |
| Aspartate | Asp | D |
| Glutamate | Glu | E |
| Phenylalanine | Phe | F |
| Glycine | Gly | G |
| Histidine | His | H |
| Isoleucine | Ile | I |
| Lysine | Lys | K |
| Leucine | Leu | L |
| Methionine | Met | M |
| Asparagine | Asn | N |
| Proline | Pro | P |
| Glutamine | Gln | Q |
| Arginine | Arg | R |
| Serine | Ser | S |
| Threonine | Thr | T |
| Valine | Val | V |
| Tryptophan | Trp | W |
| Tyrosine | Tyr | Y |
| γ-carboxyglutamic acid | Gla | V |

BRIEF DESCRIPTION OF THE DRAWINGS

FIG. 7 shows the ES-MS spectrum of cathepsin G degraded rFVIIa derivatives.

FIG. 8 shows the cleavage sites in the heavy chain of rFVIIa, β, and γ exposed by activation, and δ and ε susceptible to cathepsin G catalysis (shown in the Sequence Listing as SEQ ID NO:25 and SEQ ID NO:26).

DETAILED DESCRIPTION OF THE INVENTION

Figure 1:
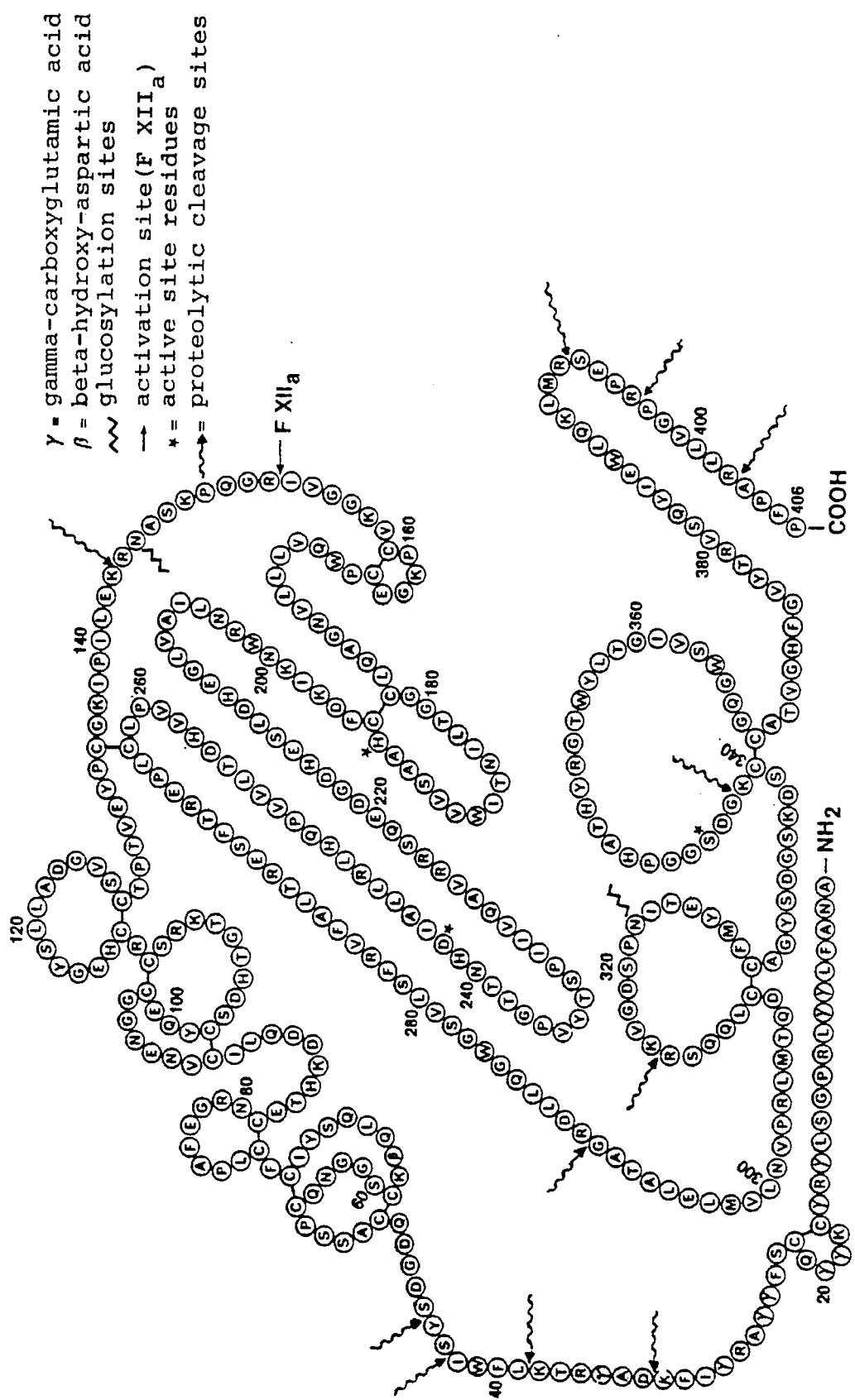
FIG. 1 illustrates the amino acid sequence given by one letter abbreviations and the tentative structure for factor Vii (SEQ ID NO:24).

The present invention is directed to a modified factor VII/VIIa being stabilized against proteolytic cleavage at a certain position(s) in the molecule, pharmaceutical compositions, and uses thereof. More specifically, the present invention provides modified factor VII/VIIa in which one or more proteolytically sensible peptide bond(s) in native factor VII/VIIa has/have been replaced by a proteolytically more stable peptide bond.

PRODUCTION OF MODIFIED FACTOR VII

The modified factor VII/VIIa of the present invention may be produced by various methods known in the art. The manipulations which result in their production can occur at the gene or protein level. Specifically, factor VII may be altered at the gene level by site-specific mutagenesis using procedures known in the art. One approach which may be taken involves the use of synthetic oligonucleotides to construct a modified factor VII with base substitutions. In one embodiment, a short oligonucleotide containing the modification is synthesized and annealed to the single stranded form of the wild-type factor VII gene (Zoller and Smith, 1984, DNA 3:479–488 and Moringa et al., 1984, Bio/Technology 2:636). The resulting short heteroduplex can serve as primer for second strand synthesis by DNA polymerase. At the 5' end, a single stranded nick is formed which is closed by DNA ligase. In another embodiment, two complementary oligonucleotides are synthesized, each containing the altered sequence. The duplex that forms after annealing these complementary oligonucleotides, can be joined to a larger DNA molecule by DNA ligase provided that the ends of both molecules have complementary single-stranded "sticky" ends.

Another approach which may be taken involves introducing a small single-stranded gap in the DNA molecule followed by mis-repair DNA synthesis i.e., the misincorporation of a non-complementary nucleotide in the gap (Botstein and Shortle, 1985, Science 229:1193). The incorporation of a thiol nucleotide into the gap may minimize the excision of the non-complementary nucleotide. Alternatively, a factor VII variant may be prepared by chemically synthesizing the DNA encoding the factor VII variant using procedures known in the art (see, for example, Froehler, 1986, Nucl. Acids Res. 14:5399–5407 and Caruthers et al., 1982, Genetic Engineering, J. K. Setlow and A. Hollaender eds., Plenum Press, New York, vol. 4, pp. 1–17). In a preferred embodiment, fragments of the variant factor VII are chemically synthesized and these fragments are subsequently ligated together. The resulting modified factor VII strands may be amplified using procedures known in the art, e.g. PCR technology and subsequently inserted into a cloning vector as described in Section 5.1., supra. In a specific embodiment, site specific mutants may be created by introducing mismatches into the oligonucleotides used to prime the PCR amplification (Jones and Howard, 1990, Biotechniques 8:178–180).

Manipulations of the factor VII sequence may be carried out at the protein level. Any of numerous chemical modifications may be carried out by known techniques including but not limited to specific chemical cleavage by cyanogen bromide, trypsin, chymotrypsin, papain, V8 protease, NaBH$_4$; acetylation, formylation, oxidation, reduction; etc. Alternatively, the variant factor VII protein may be chemically synthesized using procedures known in the art, such as commercially available peptide synthesizers and the like. Such standard techniques of polypeptide synthesis can be found described in such publications as Merrifield, 1963, J. Chem. Soc. 85:2149–2154 and Hunkapillar et al., 1984, Nature (London) 310:105–111).

The identified and isolated gene or cDNA can then be inserted into an appropriate cloning vector. A large number of vector-host systems known in the art may be used. Possible vectors include, but are not limited to, cosmids, plasmids or modified viruses, but the vector system must be compatible with the host cell used. Such vectors include, but are not limited to, bacteriophages such as lambda derivatives, or plasmids such as pBR322, pUC, pGEM1®, or Bluescript® plasmid derivatives. Recombinant molecules can be introduced into host cells via transformation, transfection, infection, electroporation, etc.

The factor VII gene is inserted into a cloning vector which can be used to transform, or infect appropriate host cells so that many copies of the gene sequences are generated. This can be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and factor VII gene may be modified by homopolymeric tailing.

In specific embodiments, transformation of host cells with recombinant DNA molecules that incorporate an isolated factor VII gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

After the factor VII-containing clone has been identified, grown, and harvested, its DNA insert may be characterized using procedures known in the art. The cloned DNA or cDNA corresponding to the factor VII gene can be analyzed by methods including but not limited to Southern hybridization (Southern, 1975, J. Mol. Biol. 98:503–517), restriction endonuclease mapping (Maniatis et al., 1989, Molecular Cloning, A Laboratory Manual, Cold Spring Harbor Laboratory, Cold Spring Harbor, N.Y.), and DNA sequence analysis. DNA sequence analysis can be performed by any techniques known in the art, including but not limited to chemical methods (Maxamand Gilbert, 1980, Meth. Enzymol. 65:499–560), enzymatic methods (see, for example, Innes, 1988, Proc. Natl. Acad. Sci. U.S.A. 85:9436; Tabor and Richardson, 1987, Proc. Natl. Acad. Sci. U.S.A. 84:4767; and Sanger et al., 1977, Proc. Natl. Acad. Sci. U.S.A. 74:5463), or the use of an automated DNA sequenator (see, for example, Martin et al., 1985, Bio/Technology 3:911–915).

EXPRESSION OF MODIFIED FACTOR VII

After screening *E. coli* cells, the modified factor VII gene is isolated and recloned into a suitable expression vector. The expression vector is then transfected into an appropriate host cell which when cultured in a suitable culture medium expresses and secretes the modified factor VII which after recovery from the culture medium, is converted into the corresponding modified factor VIIa by known means.

Various host cells may be used including mammalian cells, yeast and other fungi, and bacteria. However, mammalian cells are preferred. A particularly preferred mammalian cell line is the BHK cell line tk$^-$ts13 (Waechter and Basserga, 1982, Proc. Natl. Acad. Sci. U.S.A. 79:1106–1110). Methods for expressing cloned genes in each of these hosts are known in the art, vide for instance EP published patent application no. 200,421 (expression of factor VII and IX in mammalian cells), EP published patent application no. 200,421 (expression of factor VII and IX in mammalian cells), EP published patent application no. 191, 606 (expression of protein C in bacterial cells) and EP published patent application no. 167,420 (expression of factor IX in yeast).

For expression of modified factor VII according to the invention in cultured mammalian cells, expression vectors containing cloned modified factor VII sequences are introduced into the cells by appropriate transfection techniques, such as calcium phosphate-mediated transfection (Graham and Van der Eb, 1973, Virology 52:456–467; as modified by Wigler et al., 1980, Proc. Natl. Acad. Sci. U.S.A. 77:3567–3570). Electroporation transfection technique may also be used (Neuman et al., 1982, EMBO J. 1:841–845). A DNA-calcium phosphate precipitate is formed, and this precipitate is applied to the cells. A portion of the cells take up the DNA and maintain it inside the cell for several days. A small fraction of the cells integrate the DNA into the genome of the host cell. These integrants are identified by cotransfection with a gene that confers a selectable (phenotype selectable) marker. A preferred selectable marker is the mouse dihydrofolate reductase (DHFR) gene, which imparts cellular resistance to the drug methotrexate (MTX). After the host cells have taken up the DNA, drug selection is applied to select for a population of cells that are expressing the selectable marker in a stable faction.

PURIFICATION OF MODIFIED FACTOR VII

Modified factor VII produced by the transfected cells may be removed from the cell culture media by adsorption to barium citrate. Spent medium is mixed with sodium citrate and barium chloride and the precipitate is collected. The precipitated material may then be assayed for the presence of the appropriate clotting factor. Further purification may be achieved through immunoadsorption. It is preferred that the immunoadsorption column comprise a high-specificity monoclonal antibody. Alternatively, purification of the barium citrate precipitated material may be accomplished by more conventional biochemical methods or by high-performance liquid chromatography (HPLC).

Conversion of single-chain modified factor VII to active two-chain modified factor VIIa may be achieved using factor XIIa as described by Hedner and Kisiel (1983, J. Clin.

Invest. 71: 1836–1841), or with other proteases having trypsin-like specificity (Kisiel and Fujikawa, Behring Inst. Mitt. 73: 29–42, 1983). Alternatively modified factor VII may be activated by passing it through an ion-exchange chromatography column, such as mono Q® (Pharmacia Fire Chemicals) or the like (Bjoern et al., 1986, Research Disclosures 269:564–565).

USES FOR MODIFIED FACTOR VII/VIIa

The modified factor VII/VIIa of the present invention may be used for the treatment of a bleeding disorder, e.g. patients who have developed inhibitors to factor VIII, and platelet disorders including but not limited to thrombocytopenia, yon Willebrand's disease and others typically present in association with severe tissue damage in a pharmaceutical composition with an acceptable carrier. The pharmaceutical carriers may be such physiologically compatible buffers as Hank's or Ringer's solution, physiological saline, a mixture consisting of saline and glucose. The modified factor VII/VIIa produced by the methods of the present invention can be mixed with colloidal-like plasma substitutes and plasma expanders such as linear polysaccharides (e.g. dextran), hydroxyethyl starch, balanced fluid gelatin, and other plasma proteins. Additionally, the modified factor VII/VIIa may be mixed with water soluble, physiologically acceptable, polymeric plasma substitutes, examples of which include polyvinyl alcohol, poly(ethylene oxide), polyvinylpyrrolidone, and ethylene oxide-polypropylene glycol condensates. Techniques and formulations for administering the compositions comprising the factor VII/VIIa generally may be found in Remington's Pharmaceutical Sciences, Meade Publishing Col., Easton, Pa., latest edition.

The following examples are offered by way of illustration and not by way of limitation.

EXAMPLE 1

Production of Modified Factor VIIa in Which Lys(32) has been Replaced with Gln (Factor VIIa(Gln(32))

The oligonucleotide (I) with this change is a 27-mer with changes at nucleotide position 228 which destroy a BglII site without changing the amino acid and at position 235 changing amino acid Lys(32) to Gln and is shown below.

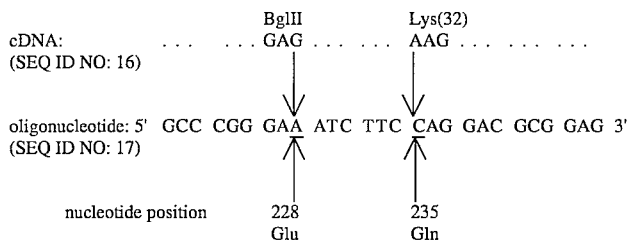

RECLONING FACTOR VII cDNA

Factor VII cDNA with a 38 amino acid long leader (Berkner, K. L. et al., Cold Spring Harbor Symposium on Quantitative Biology, Vol. LI, 531–541, 1986) was cloned in the EcoRI site of pGEM3 vector (Promega Biotec) and propagated in E. coli MC 1061 (dam$^+$) or MC 1000 (dam$^-$) bacteria strain.

Briefly, plasmid FVII (565+2463 pDK) was cut with EcoRI and the Factor VII cDNA was ligated to EcoRI cut pGEM3. The construction of plasmid FVII (565+2463)/pDX is described in EP patent application No. 86302855.1. The plasmid has also been deposited at American Type Culture Collection (ATTC No. 40205).

Restriction enzymes were obtained from Bethesda Research Laboratories (BRL), New England Biolabs, and Stratagene and were used as indicated by the producer, unless otherwise stated, oligonucleotides were synthesized on an automatic DNA synthesizer using phosphoramidite chemistry on a controlled pore glass support (Beaucage and Caruthers, 1981, Tetrahedron Letters 22, 1859–1869). E. coli cells were transformed as described by Maniatis et al. (Molecular Cloning: A Laboratory Manual, Cold Spring Harbor Laboratory, 1982).

Figure 2:
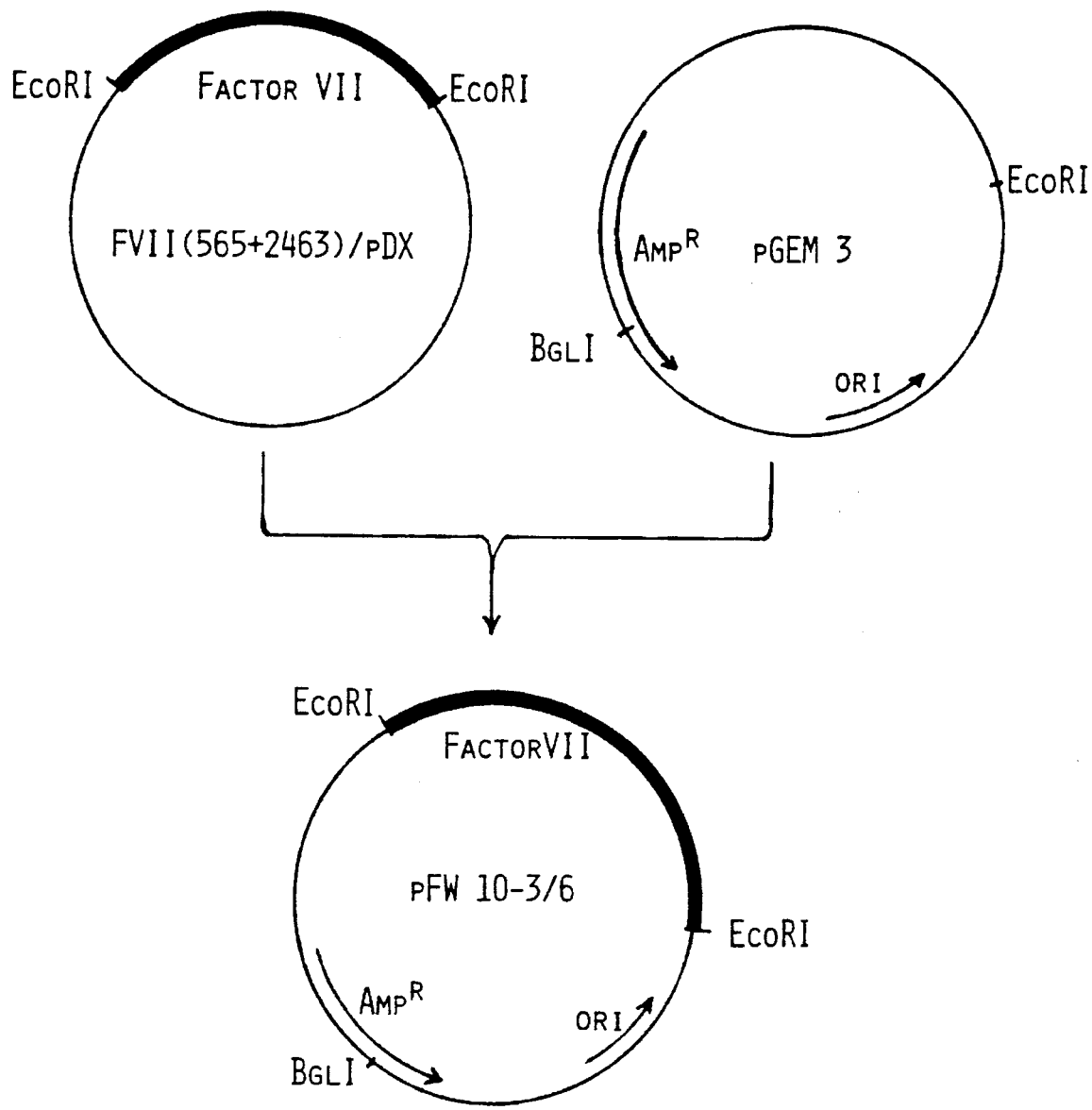
FIG. 2 illustrates the construction of plasmid pFW10-3/6.

Small and large scale DNA preparations were prepared as described in, for example, Maniatis et al., Molecular Cloning, A Laboratory Manual, Cold Spring Harbor 1982. One of these plasmid preparations is termed pFW 10-3/6. The construction of pFW 10-3/6 is illustrated in FIG. 2.

ADDITION OF 5' PHOSPHATE GROUPS TO OLIGONUCLEOTIDES

Addition of either labelled or unlabelled phosphate groups to oligonucleotides was carried out as described (Maniatis et al., 1982, Molecular Cloning: A Laboratory Manual, Cold Spring Harbor Laboratory).

OLIGONUCLEOTIDE DIRECTED SITE-SPECIFIC MUTAGENESIS USING DOUBLE-STRANDED PLASMID DNA

The site-directed mutagenesis reaction was carried out by modifying the method by Morinaga et al. 1984 (BIO/TECHNOLOGY 2:636). Plasmid pFW10-3/6 containing FVII cDNA was digested with BglI, a unique site int he plasmid. This cleavage generated fragment A) shown in FIG. 3 and FIG. 4 destroying the ampicillin resistance. Fragment A) was purified by electroelution from agarose gel and treated with calf intestinal alkaline phosphatase (CIAP) as described in Maniatis et al. as above.

Figure 3:
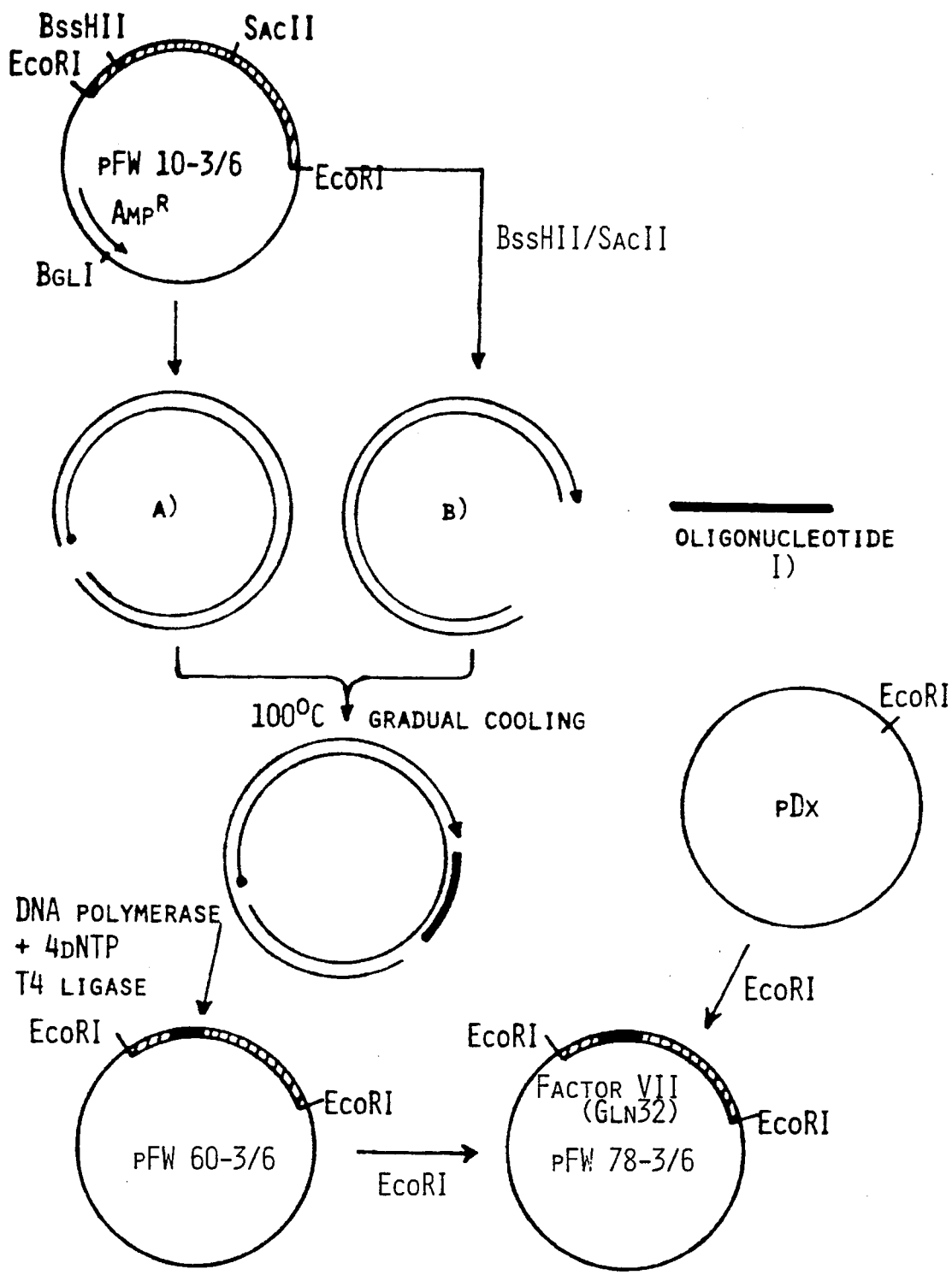
FIG. 3 illustrates the construction of plasmid pFW60-3/6.

Another sample of pFW 10-3/6 was digested with BssHII and SacII generating fragment B) in FIG. 3 with a window of 575 bp in the FVII cDNA. Fragment B) was purified by electroelution from agarose gel after electrophoresis.

(I)

Fragments A) and B) were further purified by several phenol extractions, phenol/chloroform (1:1, v/v) and chloroform/isoamyl alcohol (24:1, v/v) extractions, precipitated with 0.3M Na-acetate and 70% (v/v) ethanol and dissolved in TED (10 mM Tris, 1 mM EDTA, pH 7.6).

Figure 6:
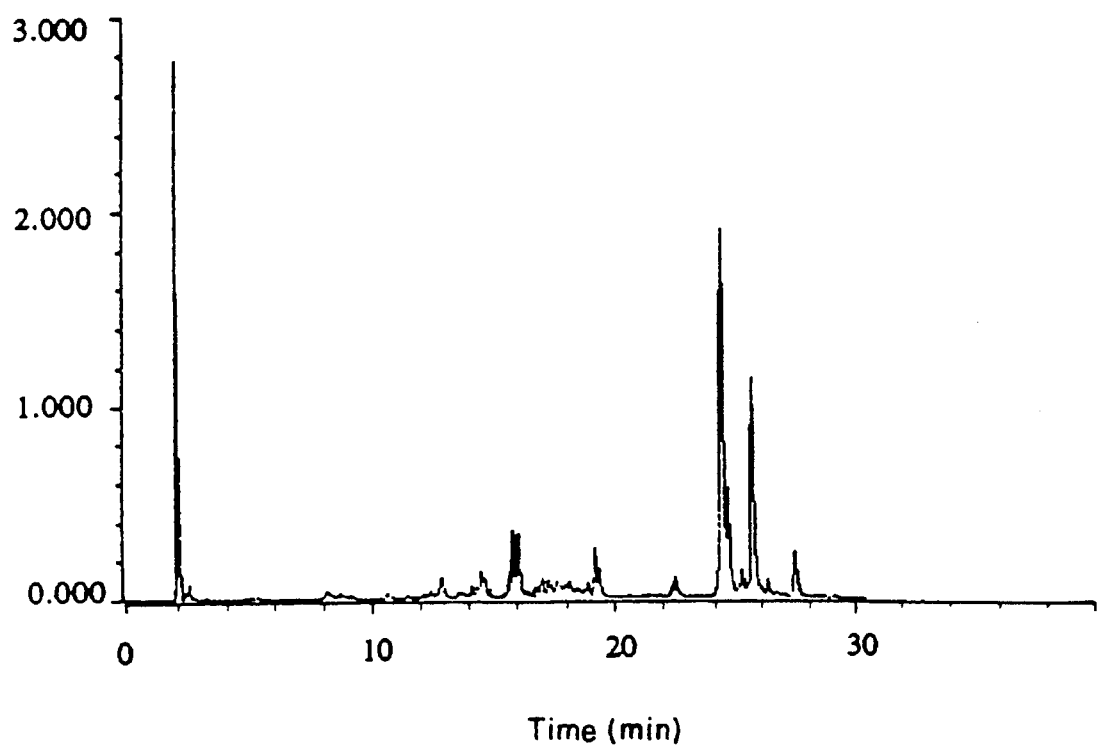
FIG. 6 shows reversed phase HPLC of cathepsin G treated recombinant Factor VIIa (rFVIIa).

Then 0.1–0.15 pmol of both fragment A) and B) were mixed with 25 pmol of the phosphorylated synthetic oligonucleotide I) shown in FIG. 6 in an Eppendorf tube. Subsequently, 10 µl of 5×polymerase-ligase buffer (0.5M NaCl, 10 mM Tris-HCl, pH 7.5, 40 mM MgCl$_2$, 5 mM 2-ME) was added.

From the final mixture, 15 μl samples were removed and stored on ice until later use as marker in gel electrophoresis. The remaining mixture was incubated in a boiling water bath for 4 min. to denature the DNA fragments. After incubation, the mixture was gradually cooled. Upon reannealing, heteroduplexes were formed and using agarose gel electrophoresis. The formation of a new circular DNA with the correct mutation was demonstrated by comparison with the non-heated sample from above.

Then, 10 μl of the four deoxyribonucleotide triphosphate (2.5 mM each), 3μl of 20 mM ATP, 1 μl of Klenow fragment of DNA polymerase I (5 U/μl) and 1 μl of T4 DNA ligase (10 U/μl) were added to the mixture (20 μl) of heteroduplexes (final volume 40 μl). The final mixture was incubated at 12° C. overnight.

Transformation of *E. coli* MC 1061 and MC 1000 with the incubation mixture resulted in ampicillin resistant transformants. Transformants carrying the modified Factor VII gene were selected by colony hybridization (Maniatis et al. ) with the 5'-$^{32}$P-labelled 27-mer and 21-mer synthetic oligonucleotides.

After retransformation, plasmid DNA was purified from selected colonies, analyzed, and sequenced (by the Maxam-Gilbert method and the dideoxy method) to verify the mutation caused by the synthetic oligonucleotide.

The construction of plasmid pFW 60-3/6 harboring a modified Factor VII gene in which Lys(32) has been replaced with Gln is illustrated in FIG. 3.

pFW 60-3/6 was digested with EcoRI and the Eco RI-EcoRI factor VII fragment was ligated into EcoRI cut pDx plasmid to obtain plasmid pFW 78-3/6 harboring the factor VII(Gin32) gene in the same orientation as in plasmid FVII (565+2463)/pDX. Plasmid pFW 78-3/6 was then transfected into BHKtk⁻ts13 cells following the general procedure described above.

The modified factor VII produced by the cells is then precipitated with barium citrate; purified by immunoadsorption; and activated to modified factor VIIa by passing it through an ion-exchange chromatography column as described (Bjoern et al., 1986, Res. Discl. 269:564–565).

TEST FOR ACTIVITY

As activated native factor VIIa, the activated modified factor VIIa shortened the coagulation period in a one-stage clotting assay. The activated modified factor VIIa was incubated at a concentration of approximately 0.9 mg/ml in a 10 mM Tris-HCl buffer at pH 8.5 comprising 390 mM NaCl and 5 mM EDTA. The degradation was monitored by SDS-PAGE of reduced samples. When significant degradation had occurred, an aliquot was withdrawn and applied to an HPLC column. The preparative chromatography served mainly to exclude Tris from the sample for amino acid sequencing as intact and degraded modified factor VIIa coeluted from the column. N-terminal amino acid sequencing revealed that no hydrolysis had occurred of the peptide bond between glutamine residue no. 32 and aspartic acid residue no. 33. In contrast, profound degradation at lysine residue no. 32 was observed when activated native factor VIIa was subjected to the same treatment and analysis as performed in a parallel investigation.

EXAMPLE 2

Production of a Modified Factor VIIa in Which Lys(38) has been Replaced with Thr 1(Factor VIIa(Thr 38))

By following the procedure of Section 6, supra, with the only exception that the synthetic oligonucleotide II shown below, was used instead of oligonucleotide (I), an expression plasmid was obtained harboring the mutated factor VII gene. Oligonucleotide (II) is a 21-mer with changes at nucleotide position 254 changing amino acid Lys(38) to Thr.

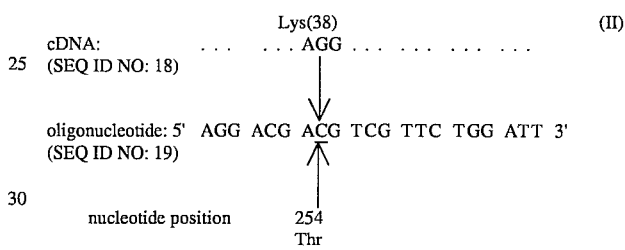

This plasmid is then transfected into BHKtk⁻ts13 cells and factor VII(Gin32, Thr38) is recovered from the cell supernatant and activated to factor VIIa(Gln32, Thr38) as described.

EXAMPLE 3

Production of a Modified Factor VIIa in which Arg(290) has been Replaced with Ser(290) (Factor VIIa(Ser(290))

Figure 4:
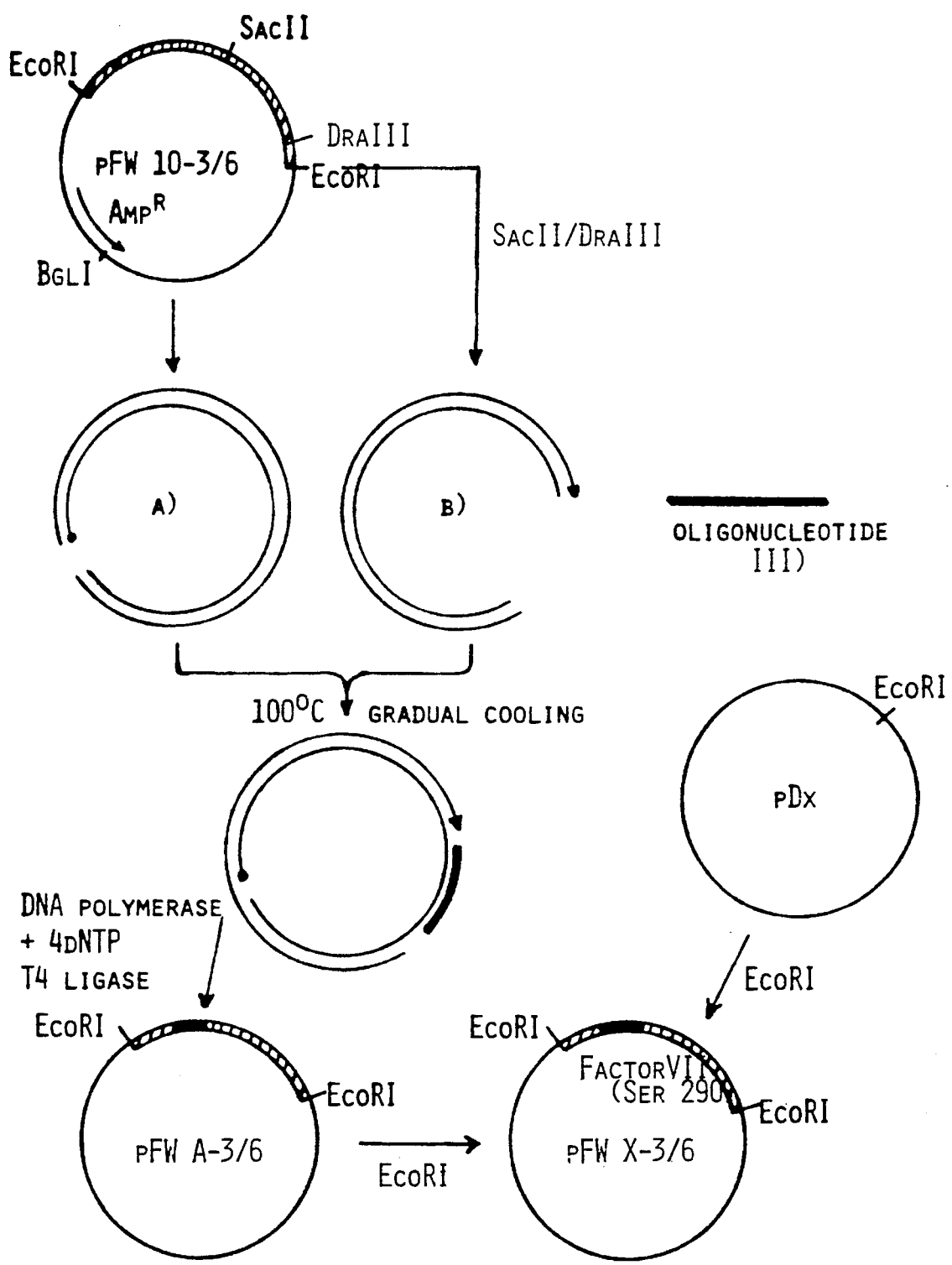
FIG. 4 illustrates the construction of plasmid pFWx-3/6.

The construction of plasmid pFW A-3/6 harboring a mutated factor VII gene in which Arg(290) has been replaced with Ser is illustrated in FIG. 4, Plasmid pFW 10-3/6 was used to produce the fragment A) of Example 1 (Section 6) and another sample of pFW 10-3/6 was digested with SacII and DraIII generating fragment B) in FIG. 4. with a window of 1366 bp in the FVII cDNA.

Fragments B) and A) were subsequently treated as described in Section 6 except for the use of oligonucleotide (III), shown below, Oligonucleotide (III) is a 27-mer with changes at nucleotide position 1009 changing the amino acid Arg (290) to Ser.

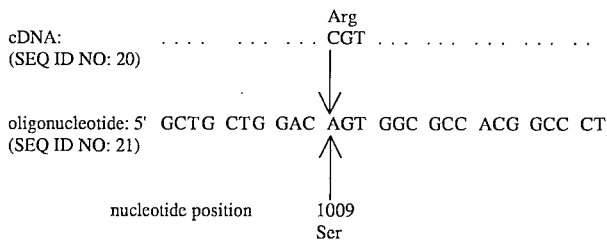

(III)

pFW A-3/6 was digested with EcoRI and the EcoRI-EcoRI factor VII fragment was ligated into EcoRI cut pDx plasmid to obtain plasmid pFW X-3/6 harboring the factor VII(Ser290) gene in the same orientation as in plasmid FVII(565+2463)/pDX, Plasmid pFW X-3/6 was then transfected into BHKtk⁻ts13 cells following the general procedure described above.

The modified factor VII produced by the cells is then precipitated with barium citrate; purified by immunoadsorption; and activated to modified factor VIIa by passing it through an ion-exchange chromatography column as described by Bjoern et al., supra.

EXAMPLE 4

Production of a Modified Factor VIIa in Which Arg(315) has been Replaced with Ser (Factor VIIA(Ser315))

By following the procedure of Example 3 (Section 8) with the only exception that the synthetic oligonucleotide (IV), shown below, was used instead of oligonucleotide (III), an expression plasmid was obtained harboring the mutated factor VII gene. Oligonucleotide (IV) is a 26-mer with changes at nucleotide position 1084 and 1086 changing amino acid Arg(315) to Ser.

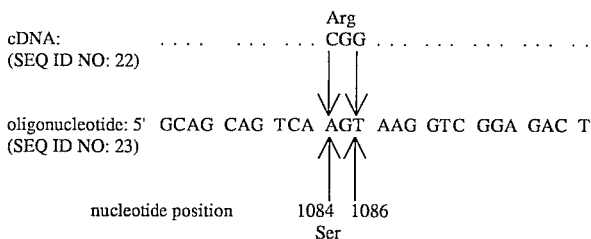

This plasmid is then transfected into BHKtk⁻ts13 cells and factor VII(Ser315) is recovered from the cell supernatant and activated to factor VIIa (Ser315) as described.

EXAMPLE 5

Determination of Active Proteolytic Cleavage Sites

Cleavage by Human Plasma Enzyme(s)

The susceptibility to cleavage(s) in the N-terminal part was demonstrated by incubating purified plasma FVII/VIIa at 4° C. in the absence of calcium ions for 2 weeks. The N-terminal amino acid sequence determination (13 cycles) showed five N-terminal amino acid sequences from the light chain starting at Ala-1 (400 pmol), Asp-33 (200 pmol), Leu-39 1600 pmol), Ser-43 (50 pmol) and Ser-45 (50 pmol), One N-terminal amino acid sequence from the heavy chain was found Ile-153 (1300 pmol), a normal proteolytic activation site, These results indicate 4 cleavage sites in the light chain, Lys-32, Lys-38, Ile-42, and Tyr-44, situated in between the Gla-domain and the EGF-like domains on the light chain (FIG. 1).

Factor VIIa Derivatives Obtained by Autolytic and Controlled Cathepsin G-Mediated Cleavage Four cleavage sites on the heavy chain have been identified: Two are susceptible to (trypsin-like catalysis) autolysis and two susceptible to (chymotrypsin-like catalysis) cathepsin G mediated lysis. Neutrophil cathepsin G initially generates a Gla-domainless FVIIa without coagulant activity. However, on extended exposure cleavage also occurs in the heavy chain, resulting in a complete loss of enzyme activity, The heavy chain cleavage might contribute to regulation of the coagulation process in vivo.

Experimental

Recombinant FVIIa (Thim et al., 1988, Biochemistry 27:7785–7793), 1 mg/ml was dialyzed against 10 mM Tris-HCl, pH 8.6, containing 75 mM NaCl and 5 CaCl₂.

(IV)

Calcium ions were complexed with EDTA, added in an excess of 5 mM, before the incubation with cathepsin G at 37° C. The final pH of the incubation mixture was 7.6. Cathepsin G was purified from human neutrophils according to the method of Baugh and Travis (1976, Biochemistry 15:836–843).

Specific clotting activity was determined in a one-stage FVII clotting assay, based on FVII immunodepleted human plasma and rabbit thromboplastin.

The substrate for amidolytic activity was S-2288 Ile-Pro-Arg-p-nitroanilide (KABI Vitrum, Sweden). The rFVIIa was diluted in 0.1M Tris-HCl, 0.1M NaCl, 5 mM CaCl₂, pH 8.3, containing 0.1% PEG-6000, and substrate added to a final concentration of 1 mM. The absorption at 405 nm was read after 30 min incubation at 37° C.

Reduction with DTT was performed overnight at room temperature in 0.3M Tris-HCl, pH 8.1 containing 6M guanidine hydrochloride. Iodoacetamide was added for caboxymethylation of free sulfhydryl groups. Excess reagents were removed by dialyses in tubing with a molecular cut-off of 3.500.

SDS-PAGE, reverse phase high performance liquid chromatography (RP-HPLC), and amino acid sequence analysis were performed as previously described (Thim et al., 1988, Biochemistry 27:7785–7793; and Thim et al., 1987, FEBS Lett. 212: 307–312).

ES-MS (electrospray mass spectrometry) analysis as performed using a API III LC/MS/MS system (Sciex, Thornhill, Ontario, Canada). The triple quadrupole instrument has a mass-to-charge (m/z) range of 2400 and is fitted a pneumatically-assisted electrospray (also referred to as ionspray) interface (Bruins et al., 1987, Anal. Chem. 59:2642–2646 and Covey et al., 1988, Rapid Commun. Mass Spectrom. 2:249–256). Sample introduction was done by a syringe infusion pump (Sage Instruments, Cambridge, Mass., through a fused capillary (75 um i.d.) with a liquid flow rate set at 0.5–1 µl/min. The instrument m/z scale was calibrated with the singly-charged ammonium adduct ions of polypropylene glycols under unit resolution.

Results

Heavy-Chain Cleavage Present After Purification and Activation

Figure 5:
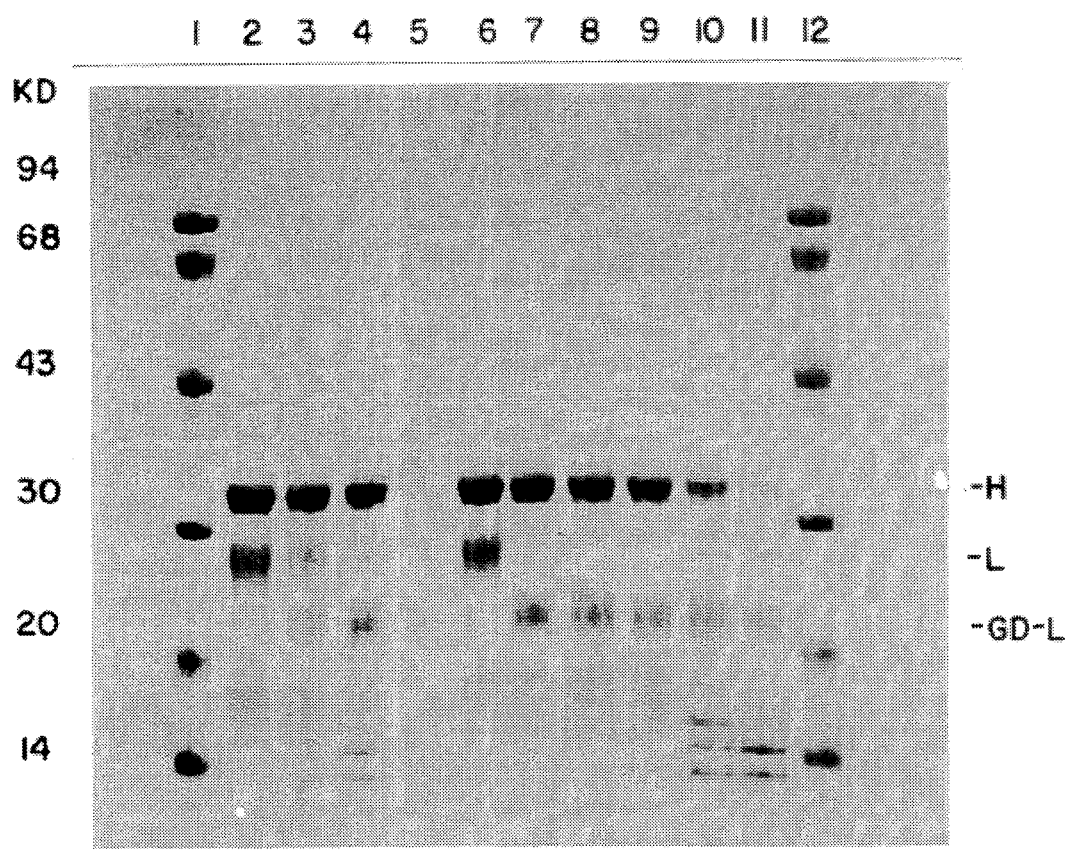
FIG. 5 shows SDS-PAGE of Factor VIIa.

FIG. 5 shows the SDS-PAGE pattern during 120 min. incubation of rFVIIa with cathepsin G in the presence and absence of calcium ions. Specifically, rFVIIa (1 mg/ml) was incubated at 37° C. in the presence (lanes 2–4) and absence (lanes 5–11) of calcium ions (5 mM $CaCl_2$) with cathepsin G (1/50 w/w). At the indicated intervals (lanes 2 and 5, 0 min.; lanes 3 and 9, 20 min.; lanes 4 and 11, 120 min.; lane 7, 10 min.; lane 10, 60 min.), aliquots were either diluted into 1% SDS, 1% DTT and boiled for SDS-PAGE, diluted in $Ca^{2+}$ containing buffer on ice for clotting analysis or diluted in substrate containing buffer for measuring amidolytic activity after 10 min. SDS-PAGE of the reduced starting material, before the incubation with Cathepsin G shows the H- and L-chain and in addition traces of four bands in the region 16–19 kd (FIG. 5, lane 2). RP-HPLC of the purified rFVIIa revealed two minor peaks eluted in front of the main protein (Thim et al., 1988, Biochemistry 27:7785–7793).

The SDS-PAGE analysis of the first of these minor peaks showed a two chain structure of 36 kd, consisting of a 16 kd band, covalently linked to the L-chain, and N-terminal amino acid sequence analysis confirmed the sequences for the intact L-and H-chain, starting at Ala-1 and Ile-153, respectively. The second minor peak contained a single peptide chain of 17 kd, with an N-terminal sequence starting at Gly-291 (see Table I, sequence A).

The remaining two bands of 19 and 17 kd (FIG. 5, lane 2) were present in the main protein peak from RP-HPLC. When the predicted residues for the L- and H-chain were disregarded, N-terminal amino acid sequencing revealed a sequence, starting at Lys-316, and corresponding to a cleavage in the third loop of the heavy chain (see Table I, sequence B).

TABLE I

AMINO ACID SEQUENCE ANALYSIS OF rFVIIA FRACTIONS FROM REVERSED PHASE HPLC

A. Minor peak

| Cycle | 1 | 2 | 3 | 4 | 5 | 6 | 7 | 8 | 9 | 10 | 11 | 12 |
|---|---|---|---|---|---|---|---|---|---|---|---|---|
| PTH-aa | Gly | Ala | Thr | Ala | Leu | Glu | Leu | Met | Val | Leu | Asn | Val |
| Yield in pmol | 169 | 164 | 46 | 140 | 124 | 117 | 125 | 117 | 124 | 87 | 128 | 121 |

B. Main peak*

| Cycle | 1 | 2 | 3 | 4 | 5 | 6 | 7 | 8 | 9 | 10 | 11 | 12 |
|---|---|---|---|---|---|---|---|---|---|---|---|---|
| PTH-aa | Lys | Val | Gly | Asp | Ser | Pro | Asn | Ile | Thr | Glu | Tyr | Met |
| Yield in pmol | 92 | — | — | 168 | 77 | 136 | — | 203 | 149 | 160 | 177 | 84 |

*In addition to the $NH_2$-terminal sequences for the L-chain (Ala—Asn—Ala—Phe—Leu—) and the H-chain (Ile—Val—Gly—Lys—), the sequence shown was recovered. In cycle 2 and 3 the heavy chain and the derivative release the same amino acids.

The observed SDS-PAGE pattern is consistent with a cleavage after Arg-290 (γ cleavage site), resulting in an L-linked fragment 153–290 (lowest band of 16 kd) and a non-covalent fragment 291–406 containing the N-linked carbohydrate at Asn-322 (band at 17 kd), and a cleavage after Arg-315, resulting in three covalently linked chains, the L chain, the fragment 153–315 (upper band of 19 kd) and the fragment 316–406 carrying the N-Glycan (band at 17 kd).

Heavy-Chain Cleavage by Cathepsin G Mediated Catalysis

In the absence of calcium ions, and a ratio of cathepsin G to rFVIIa of 1:500 w/w, rFVIIa was completely converted to a Gla-domainless form within five minutes. At a higher enzyme/substrate ratio, (1:50 w/w), a rFVIIa was identified as the main product after 20 min of incubation (Nicolaisen et al., 1992, FEBS Lett. 306:157–160). Heavy chain cleavage was detectable by SDS-PAGE after 60 min of incubation, generating three chains (FIG. 5, lane 11). In the presence of calcium ions, cleavage of both the L-and H-chain was delayed (FIG. 5, lane 4).

While the tissue factor dependent clotting activity was reduced in parallel with the formation of Gla-domainless rFVIIa, the enzymatic activity towards a low-molecular substrate was lost with the cleavage of the H-chain, and 5% of the amidolytic activity of the control remained after 3 hours of incubation with cathepsin G. From FIG. 5 it is seen that the H-chain degradation fragments (15–17 kd), present before addition of cathepsin G changes position in the SDS-PAGE gel, indicating at least two cleavage sites, one in between residues 153 and 290 and another in between residues 316 and 406.

The pattern on RP-HPLC after extended cathepsin G exposure (1:50, 120 min), is shown in FIG. 6. As the GD (Gla domainless)—rFVIIa peak (Rt 27 min) diminished, two main peaks with Rt 24 and 26 min, appeared. Analyzed by SDS-PAGE, the former peak contained the Gla-domainless L chain with the 15 kd band covalently linked, and N-terminal amino acid sequence analysis confirmed the Ser-45 sequence from the L-chain and the Ile 153 sequence from the H-chain. The fragment eluted at 26 min had an N-terminal sequence starting at Ser-333 (Table II), confirming a cleavage in between residues 316 and 406, predicted from SDS-PAGE.

TABLE II

| AMINO ACID SEQUENCE ANALYSIS OF CATHEPSIN G DEGRADED RELEASE | | | | | | | | | | | | |
|---|---|---|---|---|---|---|---|---|---|---|---|---|
| Cycle | 1 | 2 | 3 | 4 | 5 | 6 | 7 | 8 | 9 | 10 | 11 | 12 |
| PTH-aa | Ser | Asp | Gly | Ser | Lys | Asp | Ser | Cys | Lys | Gly | Asp | Ser |
| Yield in pmol | 269* | 397* | 380* | 161* | 342 | 377 | 126 | — | 348* | 380* | 196 | 76 |

*The same amino acids are released from the (45–152) L-chain and/or the H-chain. The amount of Gla-domainless release present in the RP-HPLC fraction (RT 26 min) corresponded to 10% PTH—Cys is not determined.

Figure 7A:
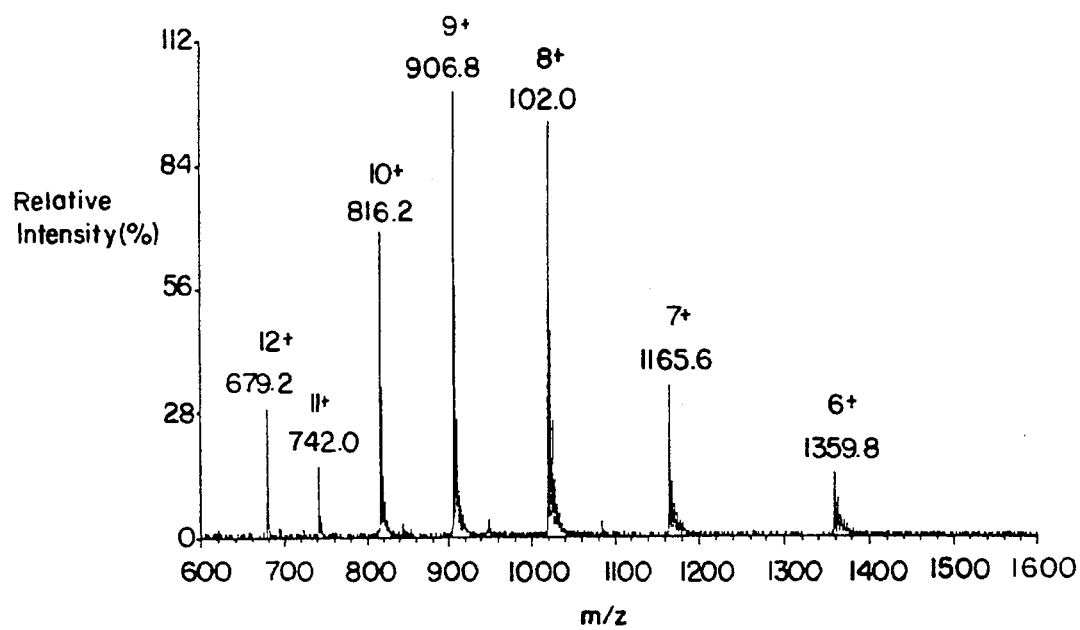
FIG. 7a shows the spectrum of the reversed phase HPLC fraction from FIG. 6, supra.
Figure 7B:
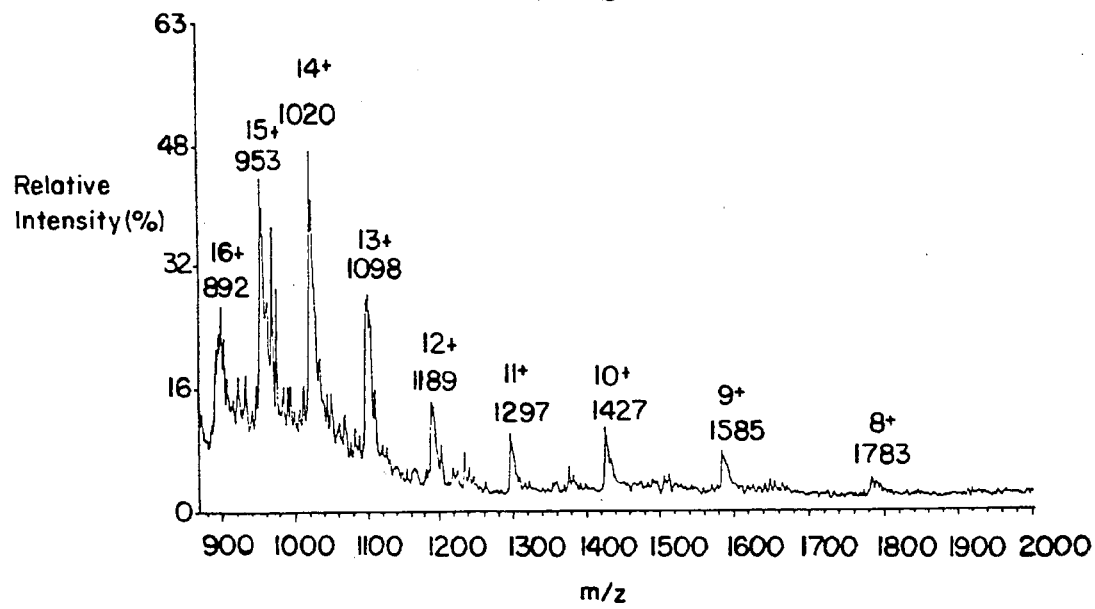
FIG. 7b shows a fraction from reversed phase HPLC of reduced and alkylated cathepsin G degraded rFVIIa.

The fragments, isolated by RP-HPLC were applied to ES-MS. The mass obtained for the fragment starting at Ser-333 was 8153 (FIG. 7a), confirming an intact C-terminus of the rFVIIa. The theoretical value, calculated from amino acid sequence of 333–406 is 8153. A fraction from RP-HPLC of the reduced and alkylated molecule gave a mass of 14259 (FIG. 7b). The calculated value for the alkylated fragment 153–278 is 14260. The cleavage between 153 and 290, predicted from the SDS-PAGE pattern, therefore occurs after Phe-278.

A heavy chain fragment, corresponding to 279–332, and containing the N-linked carbohydrate was not recovered. It might have been further degraded or lost during RP-HPLC.

Discussion

The results disclosed in Section 10.2.2., supra, indicate that cleavage occurs after Arg-290 in the human rFVIIa molecule, but also after Arg-315. The heavy chain cleavages could be demonstrated after Arg-315 and after activation, which occurred during purification. The results further indicate that the heavy-chain cleavage occurs at the two tryptic sites, exposed after the conversion of single chain to two-chain and that such cleavage can be mediated by FVIIa itself.

Cathepsin G has been shown to remove the Gla-domain of vitamin K dependent coagulation factors at a position, corresponding to Phe 40-Trp 41 in plasmid FVII (Turkingtron, 1992, Thromb. Res. 67:147–155). The results disclosed in Section 10.2.2., supra indicate that FVIIa derivatives were obtained by controlled cathepsin G cleavage, Using a higher ratio of enzyme to substrate (1/50), cleavage at Tyr 44-Ser-45 in the L-chain and on prolonged exposure, H-chain cleavage Was found. Two cleavage sites on the H-chain have been identified. One site, Tyr 332-Ser 333 occurring at a sequence identical to the L-chain cleavage at Tyr 44 (Y-S-D-G), was determined by N-terminal sequence analysis, while a second site, Phe 278-Ser 279 could be deduced from analysis of recovered fragments by ES-MS.

The accuracy of mass measurements is generally better than 0.02%, although low-intensity spectra may result in poorer mass precision. ES-MS is a very powerful tool for structural characterization, and the analysis, reported here, confirmed an intact C-terminus of the recombinant FGVIIa molecule. The 279–332 fragment was not recovered and might have been further degraded.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A native human modified factor VII/VIIa, wherein at least one lysine, arginine, isoleucine, phenylalanine or tyrosine residue selected from the group consisting of (i) lysine (38)

(ii) lysine (32)

(iii) arginine (290)

(iv) arginine (315)
(v) lysine (341)
(vi) arginine (304)
(vii) isoleucine (42)
(viii) tyrosine (44)
(ix) phenylalanine (278)
(x) tyrosine (332)

has been replaced with an amino acid which provides a proteolytically more stable peptide bond, wherein Lys(32) has been replaced with an amino acid selected from the group consisting of Gln, Glu, His, Gly, Thr, Ala and Ser.

2. The modified factor VII/VIIa according to claim 1 wherein Lys(38) has been replaced with an amino acid selected from the group consisting of Thr, Asp, Leu, Gly, Ala, Ser, Asn and His.

3. The modified factor VII/VIIa according to claim 1 wherein Lys(32) has been replaced with Gln.

4. The modified factor VII/VIIa according to claim 1 wherein Arg(290) has been replaced with an amino acid selected from the group consisting of Gly, Ala, Ser, Thr and Lys.

5. The modified factor VII/VIIa according to claim 1 wherein Arg(315) has been replaced with an amino acid selected from the group consisting of Gly, Thr, Ala, Ser and Gln.

6. The modified factor VII/VIIa according to claim 1 wherein Lys(341) has been replaced with an amino acid selected from the group consisting of Glu, Gln, Gly, Thr, Ala and Ser.

7. The modified factor VII/VIIa according to claim 1 wherein Lys(341) has been replaced with an amino acid selected from the group consisting of Glu and Gln.

8. A modified factor VII/VIIa wherein Lys(38) has been replaced with Thr and Lys(32) has been replaced with Gln.

9. A modified factor VII/VIIa wherein Arg(304) has been replaced with an amino acid selected from the group consisting of Gly, Thr, Ala, Ser and Gln.

10. A pharmaceutical composition comprising (a) a native human modified factor VIIa, wherein at least one lysine, arginine, isoleucine, phenylalanine or tyrosine residue selected from the group consisting of (i) lysine (38)
(ii) lysine (32)
(iii) arginine (290)
(iv) arginine (315)
(v) lysine (341)
(vi) arginine (304)
(vii) isoleucine (42)
(viii) tyrosine (44)
(ix) phenylalanine (278)
(x) tyrosine (332)

has been replaced with an amino acid which provides a proteolytically more stable peptide bond, wherein Lys(32) has been replaced with an amino acid selected from the group consisting of Gln, Glu, His, Gly, Thr, Ala and Ser and (b) a pharmaceutically acceptable carrier.

11. A method for the treatment of a bleeding disorder in a patient comprising administering a pharmaceutical composition comprising (a) a native human modified factor VIIa, wherein at least one lysine, arginine, isoleucine, phenylalanine or tyrosine residue selected from the group consisting of (i) lysine (38)
(ii) lysine (32)
(iii) arginine (290)
(iv) arginine (315)
(v) lysine (341)
(vi) arginine (304)
(vii) isoleucine (42)
(viii) tyrosine (44)
(ix) phenylalanine (278)
(x) tyrosine (332)

has been replaced with an amino acid which provides a proteolytically more stable peptide bond, wherein Lys(32) has been replaced with an amino acid selected from the group consisting of Gin, Glu, His, Gly, Thr, Ala and Set and (b) a pharmaceutically acceptable carrier in an amount effective to mediate blood coagulation in said patient.

12. A recombinant DNA molecule comprising a DNA sequence encoding a native human modified factor VII/VIIa, wherein at least one lysine, arginine, isoleucine, phenylalanine or tyrosine residue selected from the group consisting of (i) lysine (38)
(ii) lysine (32)
(iii) arginine (290)
(iv) arginine (315)
(v) lysine (341)
(vi) arginine (304)
(vii) isoleucine (42)
(viii) tyrosine (44)
(ix) phenylalanine (278)
(x) tyrosine (332)

has been replaced with an amino acid which provides a proteolytically more stable peptide bond, wherein Lys(32) has been replaced with an amino acid selected from the group consisting of Gln, Glu, His, Gly, Thr, Ala and Ser.

13. A cell containing the recombinant DNA molecule of claim 12.

14. A method for the production of native human modified factor VII, comprising the steps of (a) transforming a cell with a recombinant DNA molecule comprising a DNA sequence encoding a native human modified factor VII, wherein at least one lysine, arginine, isoleucine, phenylalanine or tyrosine residue selected from the group consisting of (i) lysine (38)
(ii) lysine (32)
(iii) arginine (290)
(iv) arginine (315)
(v) lysine (341)
(vi) arginine (304)
(vii) isoleucine (42)
(vii) tyrosine (44)
(ix) phenylalanine (278)
(x) tyrosine (332)

has been replaced with an amino acid which provides a proteolytically more stable peptide bond, wherein Lys(32) has been replaced with an amino acid selected from the group consisting of Gln, Glu, His, Gly, Thr, Ala and Ser;

(b) culturing the transformed cell of step (a); and (c) isolating the native human modified factor VII, expressed in the cultured transformed cell of step (b).

15. A method for the production of native human modified factor VIIa, comprising the steps of (a) transforming a cell with a recombinant DNA molecule comprising a DNA sequence encoding a native human modified factor VIIa, wherein at least one lysine, arginine, isoleucine, phenylalanine or tyrosine residue selected from the group consisting of
(i) lysine (38)
(ii) lysine (32)
(iii) arginine (290)
(iv) arginine (315)
(v) lysine (341)
(vi) arginine (304)
(vii) isoleucine (42)
(viii) tyrosine (44)
(ix) phenylalanine (278)
(x) tyrosine (332)

has been replaced with an amino acid which provides a proteolytically more stable peptide bond, wherein Lys(32) has been replaced with an amino acid selected from the group consisting of Gln, Glu, His, Gly, Thr, Ala and Ser;

(b) culturing the transformed cell of step (a); and
(c) isolating the native human modified factor VIIa, expressed in the cultured transformed cell of step (b).

* * * * *

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Glu  Glu  Ala  Phe  Glu  Ala  Leu  Glu  Ser  Ser  Thr  Ala  Thr  Asp  Val  Phe
 1              5                        10                       15
Trp  Ala  Lys  Tyr  Thr  Ala  Xaa
              20
```

( 2 ) INFORMATION FOR SEQ ID NO:2:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Glu  Glu  Ala  Arg  Glu  Ile  Phe  Lys  Asp  Ala  Glu  Arg  Thr  Lys  Leu  Phe
 1              5                        10                       15
Trp  Ile  Ser  Tyr  Ser  Asp  Gly
              20
```

( 2 ) INFORMATION FOR SEQ ID NO:3:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
Glu  Glu  Ala  Arg  Glu  Val  Phe  Glu  Asp  Ser  Asp  Lys  Thr  Asn  Glu  Phe
 1              5                        10                       15
Trp  Asn  Lys  Tyr  Lys  Asp  Gly
              20
```

( 2 ) INFORMATION FOR SEQ ID NO:4:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Glu  Glu  Ala  Arg  Glu  Val  Phe  Glu  Asx  Thr  Glu  Arg  Thr  Thr  Glu  Phe
 1              5                        10                       15
```

```
Trp Lys Gln Tyr Val Asp Gly
             20
```

( 2 ) INFORMATION FOR SEQ ID NO:5:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

```
Glu Glu Ala Lys Glu Ile Phe Gln Asn Val Asp Asp Thr Leu Ala Phe
1               5                   10                  15
Trp Ser Lys His Val Asp Gly
             20
```

( 2 ) INFORMATION FOR SEQ ID NO:6:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
Gly Tyr Lys Gly Arg Val Thr Gly Trp Gly Asn Leu Lys Glu Thr Trp
1               5                   10                  15
Thr Ala Asn Val Gly Lys Gly Gln Pro Ser Val Xaa Leu
             20                  25
```

( 2 ) INFORMATION FOR SEQ ID NO:7:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

```
Val Arg Phe Ser Leu Val Ser Gly Trp Gly Gln Leu Xaa Xaa Xaa Xaa
1               5                   10                  15
Xaa Xaa Xaa Leu Asp Arg Gly Ala Thr Ala Leu Glu Leu
             20                  25
```

( 2 ) INFORMATION FOR SEQ ID NO:8:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

```
Gln Lys Arg Gly Ile Val Ser Gly Phe Gly Arg Thr Xaa Xaa Xaa Xaa
1               5                   10                  15
Xaa Xaa Xaa Asx Glu Lys Gly Arg Gln Ser Thr Arg Leu
             20                  25
```

( 2 ) INFORMATION FOR SEQ ID NO:9:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:9:

```
Phe Gly Ser Asx Tyr Val Ser Gly Trp Gly Arg Val Xaa Xaa Xaa Xaa
1               5                   10                  15
Xaa Xaa Xaa Phe His Lys Gly Arg Ser Ala Leu Val Leu
            20                  25
```

( 2 ) INFORMATION FOR SEQ ID NO:10:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:10:

```
Gly Gln Glu Thr Leu Val Thr Gly Trp Gly Tyr Asx Xaa Xaa Xaa Xaa
1               5                   10                  15
Xaa Xaa Xaa Ser Ser Arg Glu Lys Glu Ala Lys Arg Asn
            20                  25
```

( 2 ) INFORMATION FOR SEQ ID NO:11:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:11:

```
Cys Xaa Lys Asp Ser Thr Arg Ile Xaa Xaa Xaa Xaa Arg Ile Thr Asp
1               5                   10                  15
Asn Met Phe Cys Ala Gly Tyr Lys Pro Asp Glu Gly Lys Arg Gly Asp
            20                  25                  30
Ala Cys Glu Gly Asp Ser Gly Gly Pro Phe
            35                  40
```

( 2 ) INFORMATION FOR SEQ ID NO:12:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:12:

```
Cys Leu Gln Gln Ser Arg Lys Val Gly Asp Ser Pro Asn Ile Thr Glu
1               5                   10                  15
Tyr Met Phe Cys Ala Gly Tyr Ser Xaa Xaa Asp Gly Ser Lys Xaa Asp
            20                  25                  30
Ser Cys Lys Gly Asp Ser Gly Gly Pro His
            35                  40
```

( 2 ) INFORMATION FOR SEQ ID NO:13:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:13:

```
Cys Xaa Xaa Xaa Xaa Xaa Lys Leu Ser Ser Ser Phe Ile Ile Thr Gln
 1               5                  10                      15

Asn Met Phe Cys Ala Gly Tyr Asp Xaa Xaa Thr Lys Gln Glu Xaa Asp
            20                  25                  30

Ala Cys Gln Gly Asp Ser Gly Gly Pro His
            35                  40
```

( 2 ) INFORMATION FOR SEQ ID NO:14:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:14:

```
Cys Leu Arg Xaa Ser Thr Lys Phe Thr Xaa Xaa Xaa Xaa Ile Tyr Asn
 1               5                  10                      15

Asn Met Phe Cys Ala Gly Phe His Xaa Xaa Glu Gly Gly Arg Xaa Asp
            20                  25                  30

Ser Cys Gln Gly Asp Ser Gly Gly Pro His
            35                  40
```

( 2 ) INFORMATION FOR SEQ ID NO:15:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:15:

```
Cys Ser Glu Val Met Ser Asn Met Xaa Xaa Xaa Xaa Val Ser Glu
 1               5                  10                      15

Asn Met Leu Cys Ala Gly Ile Leu Xaa Xaa Asp Gly Arg Gln Xaa Asp
            20                  25                  30

Ala Cys Glu Gly Asp Ser Gly Gly Pro Met
            35                  40
```

( 2 ) INFORMATION FOR SEQ ID NO:16:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

GCCCGGGAGA TCTTCAAGGA CGCGGAG 27

( 2 ) INFORMATION FOR SEQ ID NO:17:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

GCCCGGGAAA TCTTCCAGGA CGCGGAG 27

( 2 ) INFORMATION FOR SEQ ID NO:18:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

AGGACGAAGT CGTTCTGGAT T 21

( 2 ) INFORMATION FOR SEQ ID NO:19:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

AGGACGACGT CGTTCTGGAT T 21

( 2 ) INFORMATION FOR SEQ ID NO:20:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

GCTGCTGGAC CTGGGCGCCA CGGCCCT 27

( 2 ) INFORMATION FOR SEQ ID NO:21:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

GCTGCTGGAC ATGGGCGCCA CGGCCCT 27

( 2 ) INFORMATION FOR SEQ ID NO:22:

( i ) SEQUENCE CHARACTERISTICS:
   ( A ) LENGTH: 26 base pairs
   ( B ) TYPE: nucleic acid
   ( C ) STRANDEDNESS: single
   ( D ) TOPOLOGY: linear ( i i ) MOLECULE TYPE: cDNA ( x i ) SEQUENCE DESCRIPTION: SEQ ID NO:22:

CGAGCAGTCA CGGAAGGTCG GAGACT 26

( 2 ) INFORMATION FOR SEQ ID NO:23:

( i ) SEQUENCE CHARACTERISTICS:
   ( A ) LENGTH: 26 base pairs
   ( B ) TYPE: nucleic acid
   ( C ) STRANDEDNESS: single
   ( D ) TOPOLOGY: linear ( i i ) MOLECULE TYPE: cDNA ( x i ) SEQUENCE DESCRIPTION: SEQ ID NO:23:

CGAGCAGTCA AGTAAGGTCG GAGACT 26

( 2 ) INFORMATION FOR SEQ ID NO:24:

( i ) SEQUENCE CHARACTERISTICS:
   ( A ) LENGTH: 406 amino acids
   ( B ) TYPE: amino acid
   ( C ) STRANDEDNESS: single
   ( D ) TOPOLOGY: linear ( i i ) MOLECULE TYPE: protein ( x i ) SEQUENCE DESCRIPTION: SEQ ID NO:24:

| Ala | Asn | Ala | Phe | Leu | Tyr | Tyr | Leu | Arg | Pro | Gly | Ser | Leu | Tyr | Arg | Tyr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Cys | Lys | Tyr | Tyr | Gln | Cys | Ser | Phe | Tyr | Tyr | Ala | Arg | Tyr | Ile | Phe | Lys |
|     |     |     | 20  |     |     |     |     | 25  |     |     |     |     | 30  |     |     |
| Asp | Ala | Tyr | Arg | Thr | Lys | Leu | Phe | Trp | Ile | Ser | Tyr | Ser | Asp | Gly | Asp |
|     |     |     | 35  |     |     |     |     | 40  |     |     |     |     | 45  |     |     |
| Gln | Cys | Ala | Ser | Ser | Pro | Cys | Gln | Asn | Gly | Gly | Ser | Cys | Lys | Pro | Gln |
|     |     | 50  |     |     |     |     | 55  |     |     |     |     | 60  |     |     |     |
| Leu | Gln | Ser | Tyr | Ile | Cys | Phe | Cys | Leu | Pro | Ala | Phe | Glu | Gly | Arg | Asn |
| 65  |     |     |     |     | 70  |     |     |     |     | 75  |     |     |     |     | 80  |
| Cys | Glu | Thr | His | Lys | Asp | Asp | Gln | Leu | Ile | Cys | Val | Asn | Glu | Asn | Gly |
|     |     |     |     | 85  |     |     |     |     | 90  |     |     |     |     | 95  |     |
| Gly | Cys | Glu | Gln | Tyr | Cys | Ser | Asp | His | Thr | Gly | Thr | Lys | Arg | Ser | Cys |
|     |     |     | 100 |     |     |     |     | 105 |     |     |     |     | 110 |     |     |
| Arg | Cys | His | Glu | Gly | Tyr | Ser | Leu | Leu | Ala | Asp | Gly | Val | Ser | Cys | Thr |
|     |     | 115 |     |     |     |     | 120 |     |     |     |     | 125 |     |     |     |
| Pro | Thr | Val | Glu | Tyr | Pro | Cys | Gly | Lys | Ile | Pro | Ile | Leu | Glu | Lys | Arg |
|     | 130 |     |     |     |     | 135 |     |     |     |     | 140 |     |     |     |     |
| Asn | Ala | Ser | Lys | Pro | Gln | Gly | Arg | Ile | Val | Gly | Gly | Lys | Val | Cys | Pro |
| 145 |     |     |     |     | 150 |     |     |     |     | 155 |     |     |     |     | 160 |
| Lys | Gly | Glu | Cys | Pro | Trp | Gln | Val | Leu | Leu | Val | Asn | Gly | Ala | Gln |
|     |     |     |     | 165 |     |     |     |     | 170 |     |     |     |     | 175 |     |
| Leu | Cys | Gly | Gly | Thr | Leu | Ile | Asn | Thr | Ile | Trp | Val | Val | Ser | Ala | Ala |
|     |     |     | 180 |     |     |     |     | 185 |     |     |     |     | 190 |     |     |
| His | Cys | Phe | Asp | Lys | Ile | Lys | Asn | Trp | Arg | Asn | Leu | Ile | Ala | Val | Leu |
|     |     | 195 |     |     |     |     | 200 |     |     |     |     | 205 |     |     |     |
| Gly | Glu | His | Asp | Leu | Ser | Glu | His | Asp | Gly | Asp | Glu | Gln | Ser | Arg | Arg |

|  |  |  |  | 210 |  |  |  |  | 215 |  |  |  | 220 |  |  |
|---|---|---|---|---|---|---|---|---|---|---|---|---|---|---|---|
| Val 225 | Ala | Gln | Val | Ile | Ile 230 | Pro | Ser | Thr | Tyr | Val 235 | Pro | Gly | Thr | Thr | Asn 240 |
| His | Asp | Ile | Ala | Leu 245 | Leu | Arg | Leu | His | Gln 250 | Pro | Val | Val | Leu | Thr 255 | Asp |
| His | Val | Val | Pro 260 | Leu | Cys | Leu | Pro | Glu 265 | Arg | Thr | Phe | Ser | Glu 270 | Arg | Thr |
| Leu | Ala | Phe 275 | Val | Arg | Phe | Ser | Leu 280 | Val | Ser | Gly | Trp | Gly 285 | Gln | Leu | Leu |
| Asp | Arg 290 | Gly | Ala | Thr | Ala | Leu 295 | Glu | Leu | Met | Val | Leu 300 | Asn | Val | Pro | Arg |
| Leu 305 | Met | Thr | Gln | Asp | Cys 310 | Leu | Gln | Gln | Ser | Arg 315 | Lys | Val | Gly | Asp | Ser 320 |
| Pro | Asn | Ile | Thr | Glu 325 | Tyr | Met | Phe | Cys | Ala 330 | Gly | Tyr | Ser | Asp | Gly 335 | Ser |
| Lys | Asp | Ser | Cys 340 | Lys | Gly | Asp | Ser | Gly 345 | Gly | Pro | His | Ala | Thr 350 | His | Tyr |
| Arg | Gly | Thr 355 | Trp | Tyr | Leu | Thr | Gly 360 | Ile | Val | Ser | Trp | Gly 365 | Gln | Gly | Cys |
| Ala | Thr 370 | Val | Gly | His | Phe | Gly 375 | Val | Tyr | Thr | Arg | Val 380 | Ser | Gln | Tyr | Ile |
| Glu 385 | Trp | Leu | Gln | Lys | Leu 390 | Met | Arg | Ser | Glu | Pro 395 | Arg | Pro | Gly | Val | Leu 400 |
| Leu | Arg | Ala | Pro | Phe 405 | Pro |  |  |  |  |  |  |  |  |  |  |

( 2 ) INFORMATION FOR SEQ ID NO:25:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:25:

| Val 1 | Arg | Phe | Ser | Leu 5 | Val | Ser | Gly | Trp | Gly 10 | Gln | Leu | Leu | Asp | Arg 15 | Gly |
|---|---|---|---|---|---|---|---|---|---|---|---|---|---|---|---|
| Ala | Thr | Ala |  |  |  |  |  |  |  |  |  |  |  |  |  |

( 2 ) INFORMATION FOR SEQ ID NO:26:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:26:

| Gln 1 | Ser | Arg | Lys | Val 5 | Gly | Asp | Ser | Pro | Asn 10 | Ile | Thr | Glu | Tyr | Met 15 | Phe |
|---|---|---|---|---|---|---|---|---|---|---|---|---|---|---|---|
| Cys | Ala | Gly | Tyr 20 | Ser | Asp | Gly | Ser |  |  |  |  |  |  |  |  |